(12) United States Patent
Stalder et al.

(10) Patent No.: US 11,236,986 B2
(45) Date of Patent: Feb. 1, 2022

(54) OCT SYSTEM AND OCT METHOD

(71) Applicant: Haag-Streit AG, Koeniz (CH)

(72) Inventors: Peter Stalder, Niederhünigen (CH); Lucio Robledo, Bern (CH)

(73) Assignee: Haag-Streit AG, Koeniz (CH)

( * ) Notice: Subject to any disclaimer, the term of this patent is extended or adjusted under 35 U.S.C. 154(b) by 0 days.

(21) Appl. No.: 17/057,417

(22) PCT Filed: May 22, 2019

(86) PCT No.: PCT/EP2019/063254
§ 371 (c)(1),
(2) Date: Nov. 20, 2020

(87) PCT Pub. No.: WO2019/224270
PCT Pub. Date: Nov. 28, 2019

(65) Prior Publication Data
US 2021/0223025 A1     Jul. 22, 2021

(30) Foreign Application Priority Data

May 23, 2018   (EP) ..................................... 18173781

(51) Int. Cl.
*G01B 9/02*     (2006.01)
*A61B 3/10*     (2006.01)

(52) U.S. Cl.
CPC .......... *G01B 9/02091* (2013.01); *A61B 3/102* (2013.01); *G01B 9/02059* (2013.01); *G01B 2290/70* (2013.01)

(58) Field of Classification Search
CPC ............ G01B 9/02091; G01B 9/02059; G01B 2290/70; A61B 3/102
See application file for complete search history.

(56) References Cited

U.S. PATENT DOCUMENTS

| 5,321,501 A | 6/1994 | Swanson et al. |
| 6,385,358 B1 | 5/2002 | Everett et al. |
| 2004/0126048 A1 | 7/2004 | Dave et al. |

(Continued)

FOREIGN PATENT DOCUMENTS

| CN | 102645172 A | 8/2012 |
| CN | 102657519 A | 9/2012 |

(Continued)

OTHER PUBLICATIONS

PCT International Search Report and Written Opinion for International application No. PCT/EP2019/063254 filed May 22, 2019; dated Jul. 11, 2019; 7 pgs.

(Continued)

*Primary Examiner* — Tarifur R Chowdhury
*Assistant Examiner* — Jonathon Cook
(74) *Attorney, Agent, or Firm* — Alix, Yale & Ristas, LLP

(57) ABSTRACT

The invention relates to an OCT system with an OCT light source for emitting OCT light into an object beam path and a reference beam path. The system comprises a detector for detecting an interference signal produced by the object beam path and the reference beam path. A polarization-dependent delay element is arranged in the object beam path. The invention also relates to a corresponding OCT method. The invention allows the effects of parasitic reflections to be reduced.

13 Claims, 3 Drawing Sheets

(56) References Cited

U.S. PATENT DOCUMENTS

| | | |
|---|---|---|
| 2005/0185192 A1 | 8/2005 | Kim et al. |
| 2005/0213103 A1 | 9/2005 | Everett et al. |
| 2007/0177104 A1* | 8/2007 | Lacombe ............ A61B 3/0091 351/211 |
| 2008/0218691 A1* | 9/2008 | Fercher ................ A61B 3/102 351/205 |
| 2008/0231807 A1* | 9/2008 | Lacombe .............. A61B 3/102 351/215 |
| 2011/0051148 A1* | 3/2011 | Flanders ................ G01J 3/10 356/519 |
| 2011/0267340 A1 | 11/2011 | Kraus et al. |
| 2012/0038885 A1 | 2/2012 | Cense et al. |
| 2014/0180075 A1* | 6/2014 | Kulkarni ................ A61B 5/42 600/425 |
| 2015/0173607 A1 | 6/2015 | Hirano et al. |
| 2016/0367134 A1 | 12/2016 | Su |
| 2017/0196459 A1 | 7/2017 | Lam et al. |
| 2018/0003479 A1 | 1/2018 | Tomatsu et al. |
| 2018/0125354 A1 | 5/2018 | Pulaski et al. |
| 2020/0225021 A1 | 7/2020 | Wei et al. |

FOREIGN PATENT DOCUMENTS

| | | |
|---|---|---|
| CN | 104127168 A | 11/2014 |
| CN | 107495921 A | 12/2017 |
| EP | 1253398 A1 | 10/2002 |
| EP | 1492442 B1 | 11/2010 |
| EP | 2799807 A1 | 11/2014 |
| JP | 2003515151 A | 4/2003 |
| JP | 2007523386 A | 8/2007 |
| JP | 2013525035 A | 6/2013 |
| JP | 2016129663 A | 7/2016 |
| JP | 2017140316 A | 8/2017 |
| WO | 2015117241 A1 | 8/2015 |
| WO | 2016110917 A1 | 7/2016 |

OTHER PUBLICATIONS

Chinese Search Report for Application No. 2019800342103; Application date: May 22, 2019; dated Jan. 21, 2021; 3 pgs.
Chinese Search Report for Application No. 2019800341882, dated Apr. 1, 2021; 3 pgs.

* cited by examiner

OCT SYSTEM AND OCT METHOD

BACKGROUND

The invention relates to an OCT system comprising an OCT light source for emitting OCT light into an object beam path and a reference beam path. An interference signal generated from the object beam path and the reference beam path is picked up by a detector. The invention additionally relates to an OCT method.

Optical coherence tomography (OCT) is an imaging measurement method. OCT light is guided onto an object, in particular human tissue. Scattering centers in the object are deduced from the reflected portions of the light. To that end, the object beam path reflected back from the object is superimposed with a reference beam path. The image information is obtained by evaluating the interference signal of the two beam paths.

It may happen that the interference signal is disturbed by parasitic reflections. This means that the interference signal does not just result from light reflected back from the object to be examined, rather that the interference signal is also influenced by other light reflections, for example light reflections from optical components in the OCT beam path. The quality of the OCT signal can be adversely affected by such parasitic reflections.

US 2015/173607 A1 discloses recording a measurement with an object in the measurement region in a first step and recording a measurement without an object in the measurement region in a second step. The artefacts caused by parasitic reflections can be removed by forming the difference between the two measurements.

SUMMARY OF THE INVENTION

The invention is based on the object of presenting an OCT system and an OCT method in which the disturbing influence of parasitic reflections is reduced. Proceeding from the prior art cited, the object is achieved by the features of the independent claims. Advantageous embodiments are specified in the dependent claims.

In the case of the OCT system according to the invention, a polarization-dependent retardation element is arranged in the object beam path.

In the case of a polarization-dependent retardation element, light passing through is retarded differently depending on the polarization state. The invention has recognized that arranging a polarization-dependent retardation element in the object beam path makes it possible to differentiate the light reflected back from the object from parasitic reflections. The parasitic reflections that have not passed through the polarization-dependent retardation element differ in their polarization state from the light signal that has passed through the polarization-dependent retardation element. The polarization state in the reference beam path can be set such that the light reflected back from the object contributes strongly to the interference signal, while the influence of the parasitic reflections is small.

The beam splitter that splits the OCT light into an object beam path and a reference beam path can be a polarization-neutral beam splitter. A beam splitter is referred to as polarization-neutral if the splitter properties are independent of the polarization state of the incident light. The invention also encompasses embodiments in which the beam splitter is not polarization-neutral.

The light from the reference beam path can be caused to interfere with light from the object beam path at an interference beam splitter. The interference beam splitter can be a polarization-neutral beam splitter. The polarization-dependent retardation element can be configured such that at the interference beam splitter the polarization overlap between the light backscattered from the measurement object and the light arriving from the reference beam path is greater than the polarization overlap between the light reflected by one or more optical elements in the object beam path and the light arriving from the reference beam path. The term polarization overlap relates to the similarity of two polarization states. A pure polarization state can be represented by its Jones vector: $e=[a1e^{j\theta 1}; a2e^{j\theta 2}]$, where a1 and a2 describe the amplitudes $\theta 1$ and $\theta 2$ the phases of the two components of the electric field vector. The overlap between two polarization states is then the absolute value of the square of the inner product between the normalized Jones vectors of these two polarization states. The overlap between orthogonal polarization states (for example between linearly horizontally and linearly vertically polarized light, or between left and right circularly polarized light) is thus equal to zero. The overlap between linearly polarized light and circularly polarized light is 0.5, and the overlap between two identical polarization states is 1. The polarization overlap between the light backscattered from the measurement object and the light arriving from the reference beam path can be greater than the polarization overlap between light reflected by one or more optical elements in the object beam path and the light arriving from the reference beam path in particular by at least 0.2, preferably by at least 0.5, more preferably by at least 0.8. It is advantageous if the OCT light is polarized before entering the retardation element. It is furthermore advantageous if the OCT light is polarized before entering the beam splitter that spreads the OCT light into the object beam path and the reference beam path. In particular, the OCT light can have a pure polarization state with a degree of polarization of, for example, at least 80%, preferably of at least 90%. In one embodiment, the OCT light is linearly polarized before entering the retardation element or the beam splitter.

The OCT system can comprise a polarized light source, such that the OCT light emanating from the light source already has a polarized state. In addition or as an alternative thereto, a polarization filter can be arranged between the OCT light source and the retardation element. The term polarization filter generally denotes an optical device through which light can pass only in a polarized state.

In addition or as an alternative thereto, a first polarization controller can be arranged between the OCT light source and the polarization-dependent retardation element. The term polarization controller generally denotes a device that can set the polarization state of light in a targeted manner. A polarization controller can be embodied as a static or variable polarization controller. In the case of a static polarization controller, the polarization state is adjusted once and then no longer altered. In the case of a variable polarization controller, the polarization state can be set during operation. A variable polarization controller can be realized for example by an optical waveguide of the relevant OCT light path being laid in one or more turns and said turns being mechanically pivotable relative to other sections of the optical waveguide. In particular, the optical waveguide can comprise a plurality of sets of turns that can be pivoted independently of one another. Given a suitable configuration of the variable polarization controller, any desired changes between pure polarization states can be established in this way. The polarization controller can be designed for manual actuation, such that the polarization state can be set manually by an operator. A motor drive of the polarization controller is also possible. The first polarization controller can be used to bring the OCT light entering the polarization-dependent retardation element to a desired polarization state.

The polarization filter and/or the first polarization controller can be arranged between the OCT light source and the beam splitter in which the OCT light is split into the object beam path and the reference beam path. The beam splitter can be configured such that 50% of the input-side power is guided into the reference beam path and 50% into the object beam path. The beam splitter can be embodied as a fiber coupler, for example, to which a fourth optical waveguide coming from the OCT light source, a third optical waveguide associated with the object beam path and a second optical waveguide associated with the reference beam path are connected.

In one embodiment, the beam splitter is embodied as a 3×3 beam splitter, in which the input-side light is split among three output channels. The 3×3 beam splitter can be configured such that between 30% and 40% of the input-side power is guided to each of the output channels. Each of the channels can be used as an input channel. Irrespective of which of the channels is used as an input channel, there can be three output channels.

The polarization-dependent retardation element can be arranged such that the OCT light in the object beam path passes through it twice. The direction of propagation of the OCT light during the first passage can be opposite to the direction of propagation during the second passage. In particular, the OCT light can pass through the retardation element once on the outgoing path to the measurement object and once on the return path coming from the measurement object.

The retardation element can be configured such that the polarization state after passing through the retardation element is orthogonal to the polarization state before entering the retardation element. An interference signal can then be generated in which the contribution of the light signal coming from the measurement object is maximal and the contribution of the parasitic reflections is minimal. If the object beam path passes through the retardation element twice, then the orthogonal polarization state can result as the sum of the two passages. By way of example, the retardation element can be configured as a λ/4 plate. The retardation element can be oriented such that the linear polarization upon the first entry is rotated into a circular polarization, and so the light backscattered from the measurement object is rotated into an orthogonal linear polarization during the second passage to the retardation element. After passing through the retardation element, the object beam path can be caused to interfere with the reference beam path without further alteration of the polarization state.

The OCT system can be configured such that all optical elements that shape or deflect the object beam path on the path from the OCT light source to the measurement object are arranged between the OCT light source and the retardation element. If the object beam path can propagate freely between the retardation element and the measurement object, no further parasitic reflections can arise in this section of the object beam path. Since the parasitic reflections that arise upstream of the retardation element can be masked out of the interference signal, a good quality of the measurement signal can be achieved in this way. Glass plates of a housing through which the OCT light possibly also passes between the retardation element and the measurement object are not optical elements that shape or deflect the object beam path because the beam shape and the beam direction remain unchanged during passage through such a glass plate. If the OCT system comprises a transparent plate through which the object beam path passes between the retardation element and the measurement object, then said plate can be tilted relative to the optical axis of the object beam path, such that possible parasitic reflections are deflected to the side and do not disturb the interference signal.

Parasitic reflections can also arise in the retardation element itself. In order to prevent their disturbing the interference signal, the retardation element can be arranged such that one or more interfaces through which the object beam path passes are tilted relative to the object beam path. This may concern, in particular, the interface via which the object beam path emerges from the retardation element in the direction of the measurement object or enters the retardation element as it comes from the measurement object. If an interface is tilted relative to the object beam path, the object beam path does not impinge on the interface orthogonally, but rather at a different angle. Parasitic reflections are deflected to the side and do not disturb the interference signal.

A second polarization controller can be arranged in the reference beam path, such that the polarization state of the OCT light in the reference beam path can be adapted to the polarization state of the OCT light coming from the measurement object. Adapting means that the polarization state in the reference beam path is set such that the interference with the OCT light coming from the measurement object becomes maximal. The polarization controller can be a static polarization controller or a dynamic polarization controller. If the OCT light is linearly polarized, for example, then the OCT light coming from the measurement object and the OCT light of the reference beam path that is caused to interfere therewith can be brought to mutually parallel polarization states.

As an alternative or in addition thereto, a second polarization-dependent retardation element can be arranged in the reference beam path. Such a polarization-dependent retardation element can contribute to avoiding parasitic reflections from the reference beam path.

The OCT system can comprise one or more optical waveguides through which the OCT light passes. The optical waveguides can be embodied as monomode optical waveguides in order to prevent disturbance signals from arising within the optical waveguides. The OCT system can comprise a first fiber coupler, in which the OCT light is split into an object beam path and a reference beam path. The first fiber coupler can be a polarization-neutral fiber coupler. The interference signal can also be generated in the first fiber coupler. The direction of propagation when splitting the OCT light can be opposite to the direction of propagation when generating the interference signal.

It is also possible for the OCT system to comprise a second fiber coupler, in which the interference signal is generated. The second fiber coupler can be a polarization-neutral fiber coupler. The reference beam path can extend between the first fiber coupler and the second fiber coupler. A second optical waveguide, in which the reference beam path is guided, can be arranged between the first fiber coupler and the second fiber coupler. The length of the reference beam path can correspond to the length of the optical path between the first fiber coupler and the second fiber coupler.

The OCT system can comprise a first optical waveguide, which extends between the first fiber coupler and the second fiber coupler, wherein the first optical waveguide forms a section of the object beam path. The length of the object beam path overall can result as the sum of the length of the first optical waveguide and double the distance between the first fiber coupler and the object.

Conventional optical waveguides have the property that the polarization state of the light can change if the spatial configuration of the optical waveguide is altered. By way of example, the polarization state of the light can be influenced by whether the optical waveguide extends rectilinearly or along turns. The OCT system can comprise one or more polarization controllers in order to compensate again for such changes in the polarization state.

The OCT system can be configured such that one or more optical waveguides are embodied as polarization-maintaining optical waveguides. An optical waveguide is referred to as polarization-maintaining if, relative to the coordinate system of the optical waveguide, the polarization states at the input and at the output of the optical waveguide are coupled to one another in a fixed manner. Relative to the spatial coordinate system the polarization state can be altered by changing the spatial configuration of the polarization-maintaining optical waveguide. A polarization-maintaining optical waveguide can have a first axis and a second axis, in which the light moves at different propagation velocities (slow axis/fast axis). The first axis and the second axis can be orthogonal to one another as viewed in the cross section of the optical waveguide. The use of polarization-maintaining optical waveguides can be appropriate, in particular, if the OCT system is configured such that the spatial arrangement of components of the system relative to one another can be altered during operation. This is regularly associated with a deformation of optical waveguides, which could influence the polarization state of the OCT light in the case of conventional optical waveguides.

A fourth polarization-maintaining optical waveguide can be arranged between the OCT light source and the first fiber coupler, in which the splitting into the object beam path and the reference beam path is effected. The linear polarization state of the OCT light fed into the optical waveguide can be oriented parallel to the first axis of the fourth polarization-maintaining optical waveguide.

A first section of the object beam path can be embodied as a third polarization-maintaining optical waveguide. The OCT light of the object beam path can pass through the third polarization-maintaining optical waveguide twice with opposite directions of propagation. In this case, the OCT light can propagate in the first axis of the polarization-maintaining optical waveguide on the outgoing path to the object and can propagate in the second axis of the polarization-maintaining optical waveguide on the return path coming from the object.

A second section of the object beam path can be embodied as a first polarization-maintaining optical waveguide. The second section of the object beam path can extend between the first fiber coupler and the second fiber coupler. In the second section of the object beam path, the OCT light can propagate in the second axis of the polarization-maintaining optical waveguide.

The invention also relates to an OCT system comprising an OCT light source for emitting OCT light, comprising a first beam splitter for splitting the OCT light into an object beam path and a reference beam path, comprising a second beam splitter for generating an interference signal from the object beam path and the reference beam path, wherein the object beam path is guided between the first beam splitter and the second beam splitter through a first polarization-maintaining optical waveguide and the reference beam path is guided between the first beam splitter and the second beam splitter through a second polarization-maintaining optical waveguide, and comprising a detector for picking up the interference signal, wherein a polarization-dependent retardation element is arranged in the object beam path and wherein the OCT light, in the first polarization-maintaining optical waveguide or in the second polarization-maintaining optical waveguide, is transferred between a first axis and a second axis of the polarization-maintaining optical waveguide.

The first axis and the second axis of the polarization-maintaining optical waveguide correspond to the fast axis and slow axis, respectively. What is advantageous for this aspect of the invention is that the transfer between the first axis and the second axis is carried out in exactly one of the two polarization-maintaining optical waveguides, that is to say either in the object beam path or in the reference beam path. If the OCT light is transferred between two axes of a polarization-maintaining optical waveguide, then the polarization-maintaining optical waveguide has a first longitudinal section, in which the OCT light propagates in the first axis, and a second longitudinal axis, in which the OCT light propagates in the second axis.

The reference beam path can be embodied as a second polarization-maintaining optical waveguide. The reference beam path can extend between the first beam splitter and the second beam splitter. The first beam splitter and/or the second beam splitter can be embodied as fiber coupler(s). If the object beam path and the reference beam path extend along parallel light paths between the first fiber coupler and the second fiber coupler, then a fiber connector can be arranged in one of the light paths, said fiber connector transferring the light between the first axis and the second axis of the polarization-maintaining optical waveguide. In other words, light that is in the first axis of the polarization-maintaining optical waveguide at the input side of the fiber connector is transferred into the second axis of the polarization-maintaining optical waveguide at the output side, and vice versa. This can be done by the first section and the second section being coupled in the fiber connector such that they are rotated by 90° relative to one another. The fiber connector can be realized in the form of a plug connection. Alternatively, a fiber splice can also be used, wherein the two fiber ends to be connected are fused by means of an arc. An interferometer comprising such a fiber connector between the first fiber coupler and the second fiber coupler has independent inventive content irrespective of whether it is used in an OCT system and whether a polarization-dependent retardation element is arranged in the object beam path.

The fiber connector can be arranged in the reference beam path. It is also possible for the fiber connector to be arranged in the object beam path, specifically in particular in the section of the object beam path which is arranged between the first fiber coupler and the second fiber coupler. The OCT light then extends in the first axis of the polarization-maintaining optical waveguide in a first section of the reference beam path or of the object beam path. The OCT light extends in the second axis of the polarization-maintaining optical waveguide in a second section of the relevant beam path.

If the fiber connector is arranged in the reference beam path, then the length of the first section and the length of the second section of the reference beam path can be in a ratio to one another which corresponds to the conditions in the object beam path, such that the OCT light in both cases covers the same distance in the first axis and in the second axis. Within the meaning of the invention, such a fiber connector is a polarization controller which is initially adjusted and is then no longer altered.

The OCT system can be embodied with a wavelength-tunable light source (swept-source OCT). The OCT system can then have a first detector and a second detector in order, for the purpose of a differential measurement, to detect the phase-shifted interference signals formed at the interference beam splitter. The phase shift depends on the choice of interference beam splitter. By way of example, the phase shift of a symmetrical 2×2 beam splitter is 180°, and the phase shift of a symmetrical 3×3 beam splitter is 120°. The difference between the photocurrents can be converted into a voltage and digitized. The interference signal for a tuning process of the light source can be digitized in a spectrally resolved manner and then be transformed into a spatial signal. Alternatively, it is also possible to use a broadband light source; a spectrometer is then used as detector (spectral domain OCT).

The first detector and the second detector can be connected to a first output channel and to a second output channel of the second fiber coupler, wherein the second fiber coupler preferably forms the interference beam splitter.

It is also possible to carry out such a differential measurement with a first detector and a second detector in an OCT system in which the OCT light is split into the object beam path and the reference beam path in a 3×3 beam splitter and in which the 3×3 beam splitter simultaneously forms the interference beam splitter. The OCT light source, the first detector and the second detector can be connected on one side of the 3×3 beam splitter. The object beam path and the reference beam path can be connected on the other side of the 3×3 beam splitter. The third channel on this side of the 3×3 beam splitter can remain unused. In one embodiment, a second reference beam path is connected to the third channel, said second reference beam path preferably having a different length than the first reference beam path. In this way it becomes possible to switch between different measurement regions.

The OCT system according to the invention can be configured such that both the OCT light backscattered from the measurement object and the parasitic reflections are guided onto the detector and are detected by the detector. This is possible without any disadvantage for the quality of the OCT measurement since the parasitic reflections do not contribute to the interference signal and the stationary portions of the OCT light cancel one another out in the differential measurement. The invention accordingly makes it possible to dispense with further polarization filters upstream of the detector.

The object beam path can comprise a section in which the OCT light propagates freely, that is to say is not guided within an optical waveguide. The section can extend between an exit end of an optical waveguide and the measurement object. A collimation optical unit can be provided, such that the object beam path extends in a collimated state in a section. The OCT system can comprise an objective, such that the object beam path is focused in the region of the measurement object. The polarization-dependent retardation element according to the invention can be arranged between the objective and the measurement object.

The object beam path can be deflected in a lateral direction by a scanning device. Sectional images of the measurement object can be generated by deflection in a lateral direction. If the scanning device is designed to deflect the object beam path in two lateral directions (for example X-direction, Y-direction), a three-dimensional volume image can be constituted from a plurality of sectional images.

The scanning device can comprise two scanning mirrors, for example, which are pivotable about mutually orthogonal axes. Such an arrangement of scanning mirrors is a conventional example of a scanning device that can be used to scan a measurement object. The scanning device can be arranged between a collimation optical unit and an objective of the object beam path. The optical unit of the object beam path can be designed in a telecentric fashion, such that the scanning device is arranged at a focal point of the objective and the beam path between the objective and the measurement object is displaced in a parallel fashion during scanning.

The reference beam path can comprise a section in which the OCT light propagates freely, that is to say is not guided within an optical waveguide. The section can extend between an exit end of an optical waveguide and a mirror. A collimation optical unit can be arranged between the exit end of the optical waveguide and the mirror, such that the OCT light in a collimated state impinges on the mirror. The OCT system can comprise a first polarization-dependent retardation element and a second polarization-dependent retardation element, wherein the second polarization-dependent retardation element is arranged in said section of the reference beam path. In other embodiments, the entire reference beam path can extend within one or more optical waveguides.

The light source of the OCT system can be a swept-source light source, in which narrowband OCT light is tuned over a spectral tuning range within a tuning time. The detector can comprise photodiodes that detect the interference signal in a time-resolved manner and thus indirectly enable a spectral resolution of the interference signal. The photocurrent of the photodiodes can be converted into a voltage and digitized. The interference signal for a tuning process of the swept-source light source can be digitized in a spectrally resolved manner and can be transformed into a spatial signal. In combination with the lateral deflection of the object beam path by the scanning device, sectional images of the measurement object can be created.

The OCT system can be used for measurements on the human eye. The line width of the light source can be chosen such that structures to a distance of 40 mm from the reference point can still be detected well. The term reference point denotes a position in the object beam path for which the optical path length from the light source to the reference point and from there back again to the interference beam splitter is equal to the optical path length from the light source via the reference beam path to the interference beam splitter. The oscillation frequency of the interference signal (in a spectral representation) is a measure of the distance between the light-scattering structure and the reference point. A reference point of the OCT system can be arranged in front of the human eye.

Since, in general, it is not possible to differentiate between positive and negative frequencies, an OCT system is also sensitive for structures that lie on the side of the reference point facing the measuring device. Optical elements in the object beam path can be at the same distance from the reference point as specific scattering centers of the eye, which is why the parasitic reflections at these optical elements generally have disturbance potential.

The beam path of the OCT system can also contain further components in addition to those mentioned. By way of example, for swept-source OCT between the OCT light source and the splitting into object beam path and reference beam path by a beam splitter, a portion of the OCT light can be coupled out in order to generate therefrom a clock signal for the digitization of the interference signal.

The invention additionally relates to an OCT method in which OCT light is emitted. The OCT light is split into an object beam path and a reference beam path. An interference signal generated from the object beam path and the reference beam path is picked up by a detector. The OCT light is guided through a polarization-dependent retardation element arranged in the object beam path.

The method can be developed with further features described in the context of the system according to the invention. The system can be developed with further features described in the context of the method according to the invention.

BRIEF DESCRIPTION OF THE DRAWINGS

The invention is described by way of example below on the basis of advantageous embodiments with reference to the accompanying drawings, in which.

DETAILED DESCRIPTION

Figure 1:
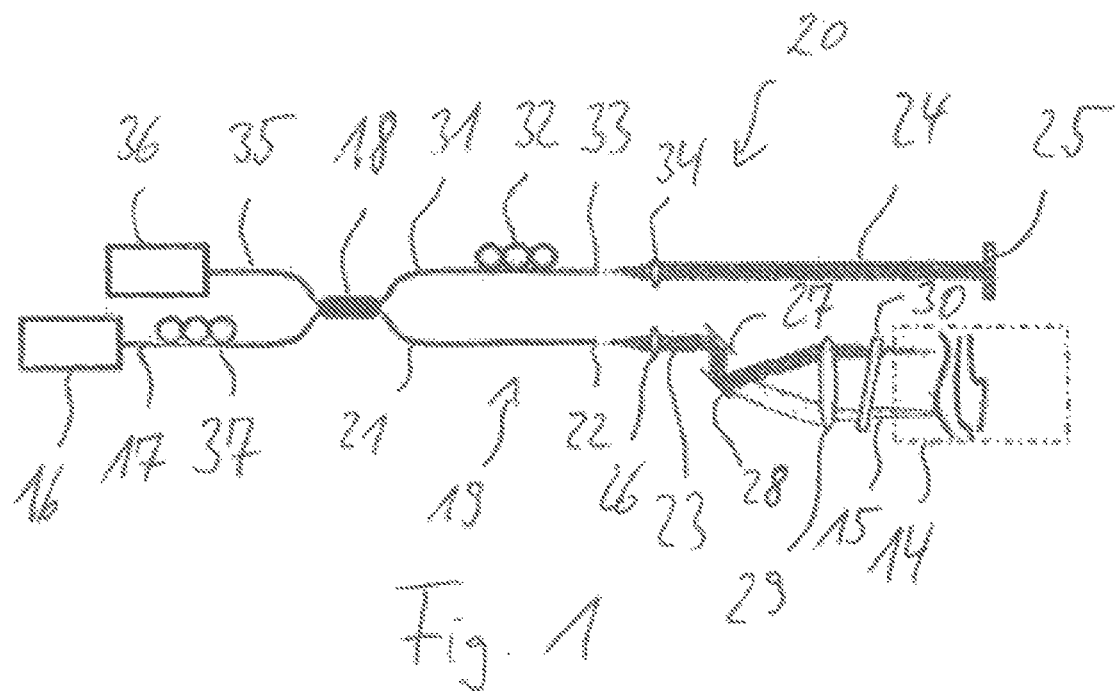
FIG. 1: shows a first embodiment of an OCT system according to the invention.

An OCT system shown in FIG. 1 serves for examining a measurement object 14 in the form of a human eye. By virtue of OCT light 15 being directed onto the measurement object 14, image information is obtained, which extends along the axis of the OCT beam into the depth of the measurement object 14. By virtue of the OCT beam being scanned over the measurement object 14 in a direction perpendicular thereto, a three-dimensional image of the measurement object 14 can be obtained from a multiplicity of individual measurement recordings.

The OCT system comprises an OCT light source 16, embodied as a swept-source light source. The swept-source light source 16 generates narrowband light that is spectrally tunable. That is to say that at each instant narrowband light is emitted, the frequency of which changes over time, such that the swept-source light source is tuned over a frequency range during a tuning time.

The OCT light 15 emitted by the OCT light source 16 is linearly polarized and is fed into a fourth optical waveguide 17, embodied as a monomode optical waveguide. The fourth optical waveguide 17 extends to a polarization-neutral fiber coupler 18, in which the OCT light 15 from the fourth optical waveguide 17 is split into an object beam path 23 and a reference beam path 24. The object beam path 23 extends along an object arm 19 as far as the measurement object 14. The reference beam path 24 extends along a reference arm 20 as far as a reference mirror 25.

The object arm 19 comprises a third optical waveguide 21, which extends from the polarization-neutral fiber coupler 18 as far as an exit end 22. At the exit end 22, the object beam path 23 emerges from the third optical waveguide 21 in a divergent state and is brought to a collimated state by a collimation lens 26.

A scanning device comprises two scanning mirrors 27, 28, which are pivotable about two mutually orthogonal axes. The object beam path 23 is guided to an objective 29 via the scanning device 27, 28. The object beam path 23 passes through the objective 29 and is focused in the region of the measurement object 14.

The direction from which the object beam path 23 impinges on the objective 29 changes by means of pivoting of the scanning mirrors 27, 28. Since the second scanning mirror 28 is arranged at the focal point of the objective 29, the beam path 23 extends between the objective 29 and the measurement object 14 parallel to the optical axis of the objective 29 independently of the position of the scanning device 27, 28. Between the objective 29 and the measurement object 14, the object beam path 23 passes through a polarization-dependent retardation element 30 in the form of a λ/4 plate.

OCT light reflected back from the measurement object 14 moves with an opposite direction of propagation along the object arm 19 back to the polarization-neutral fiber coupler 18.

The reference arm 20 comprises a second optical waveguide 31, which extends from the fiber coupler 18 via a second polarization controller 32 to an exit end 33. The reference beam path 24 emerging from the exit end 33 in a diverged state impinges on a collimation lens 34. From the collimation lens 34, the reference beam path 24 propagates in a collimated state to the reference mirror 25. The OCT light reflected by the reference mirror 25 moves with an opposite direction of propagation along the reference arm 20 back to the fiber coupler 18.

The reference mirror 25 is arranged such that the optical path between the fiber coupler 18 and the reference mirror 25 in the reference arm 20 is of exactly the same length as the optical path in the object arm 19 between the fiber coupler 18 and a reference point in the measurement object 14. Since the OCT light has covered the same optical path distance along the object arm 19 and the reference arm 20, an interference signal arises when the object beam path 23 and the reference beam path 24 are recombined in the fiber coupler 18. The interference signal is all the stronger, the more OCT light is reflected back from a specific structure within the measurement object 14. Scattering centers within the measurement object 14 can thus be identified by the evaluation of the interference signal.

If a scattering center is arranged precisely at the reference point of the object beam path, then the optical path length of the object beam path 23 and that of the reference beam path 24 are exactly equal, thus resulting in a standing interference signal. If the scattering center is at a distance from the reference point, then the interference signal oscillates (in a spectral representation), the frequency becoming all the greater, the greater the distance with respect to the reference point.

The interference signal is guided to a detector 36 via a further optical waveguide 35. The interference signal is picked up by the detector 36 and converted into spatially resolved image information.

The line width of the OCT light source 16, that is to say the instantaneous spectral width of the emitted light, is small enough that structures that are at a distance of 40 mm, for example, from the reference point can still be detected well. Such a measurement range enables recordings of a human eye to be captured using the OCT system according to the invention. In this case, the reference point can be just in front of the eye, such that all structures of the eye lie on the other side of the reference point. Since it is not possible to differentiate between positive and negative distances from the reference point in the interference signal, it is desirable to avoid reflections arranged upstream of the reference point. This applies, in particular, to reflections at such optical elements of the object arm 19 which are at a distance from the reference point that is smaller than the measurement depth of the OCT system. In the exemplary embodiment in accordance with FIG. 1, for example, parasitic reflections from the retardation element 30 or from the objective 29 can corrupt the measurement signal from the measurement object 14.

The invention is based on the concept of reducing the effects of such parasitic reflections by the measurement signal being put into a different polarization state than the parasitic reflections. What can be achieved by suitable setting of the polarization state in the reference beam path is that a maximum interference signal results from the OCT light reflected back from the measurement object 14, while at the same time the interference signal generated by the parasitic reflections is minimal.

The polarization state of the OCT light emitted by the OCT light source 16 is set by a first polarization controller 37 such that the light emerging at the exit end 22 of the third optical waveguide 21 is purely linearly polarized. The linear polarization state is maintained until passage through the λ/4 plate 30. In this case, the λ/4 plate is oriented (rotated) such that after the OCT light has passed through the λ/4 plate twice with an opposite direction of propagation, the OCT light is still purely linearly polarized, but the direction of the linear polarization is orthogonal to the original linear polarization. This is typically the case if the angle between the linear polarization at the entrance into the plate and the crystal-optical axis of the plate is 45°.

By contrast, the parasitic reflections from the optical elements of the object arm 19, which have not passed through the λ/4 plate 30, still have the original linear polarization state. The linear polarization state of the parasitic reflections is thus orthogonal relative to the linear polarization state of the OCT light reflected back from the measurement object 14.

The linear polarization state of the reference beam path 24 is set by the second polarization controller 32 such that upon the superimposition of the object beam path 23 and the reference beam path 24 in the fiber coupler 18, the linear polarization of the reference beam path 24 is parallel to the linear polarization of the OCT light coming from the measurement object 14. The OCT light reflected back from the measurement object 14 thus generates a maximum interference signal, while at the same time the interference signal generated by the parasitic reflections is minimal.

Parasitic reflections that occur when the OCT light emerges from the λ/4 plate 30 in the direction of the measurement object 14 cannot be eliminated in this way. The λ/4 plate 30 is therefore tilted relative to the optical axis of the objective 29, such that these parasitic reflections are not guided in the direction of the fiber coupler 18, but rather are deflected to the side.

Figure 2:
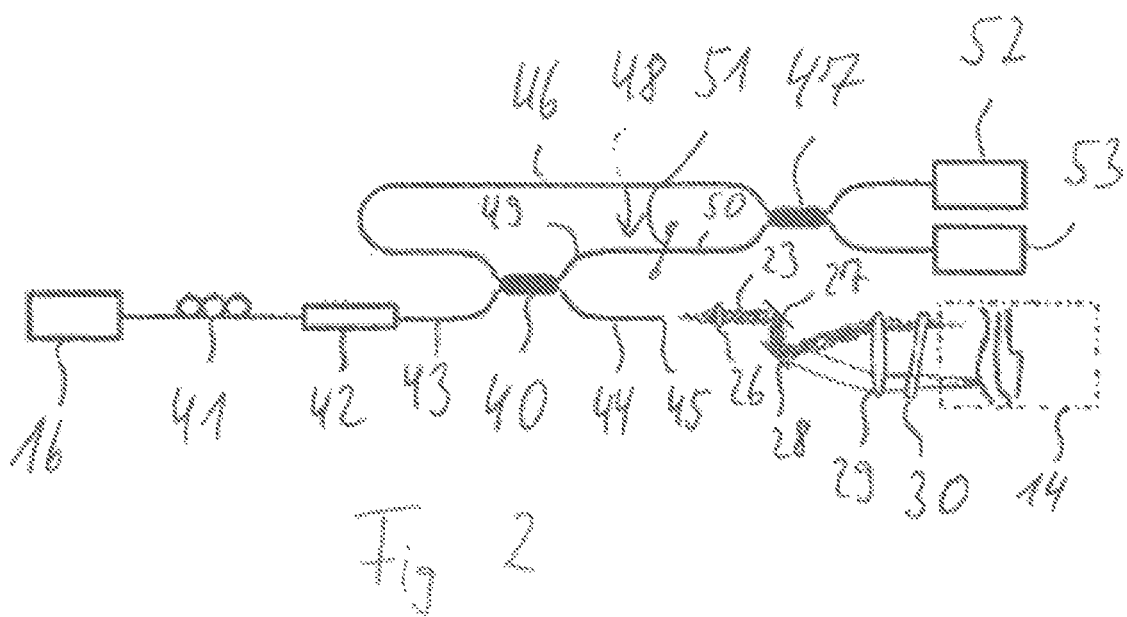
FIG. 2: shows a second embodiment of an OCT system according to the invention.

In the exemplary embodiment in accordance with FIG. 2, the OCT light source 16 is likewise embodied as a swept-source light source that emits linearly polarized OCT light. A polarization controller 41 and a polarization filter 42 are arranged between the OCT light source 16 and a first fiber coupler 40. The polarization filter 42 is designed such that it allows passage only of such light which is linearly polarized in a specific direction. The polarization state of the OCT light is set by the polarization controller 41 such that it corresponds to the linear polarization direction of the polarization filter 42. In other words, the polarization controller 41 is set such that the maximum quantity of light emerges at the output of the polarization filter 42.

A fourth optical waveguide 43, embodied as a polarization-maintaining optical waveguide, extends between the polarization filter 42 and the first fiber coupler 40. The polarization-maintaining optical waveguide 43 is connected to the polarization filter 42 such that the entire light is fed into the fast axis 62 of the optical waveguide 43.

In the first fiber coupler 40, the OCT light is split into the object beam path 23 and the reference beam path 24. In the object arm 19, a third polarization-maintaining optical waveguide 44 extends between the first fiber coupler 40 and an exit end 45. The third polarization-maintaining optical waveguide 44 is connected to the first fiber coupler 40 such that the fast axes 62 of the optical waveguides 43, 44 correspond. The OCT light from the fast axis 62 of the fourth polarization-maintaining optical waveguide 43 thus passes over to the fast axis 62 of the third polarization-maintaining optical waveguide 44.

The components of the object arm 19 between the exit end 45 of the optical waveguide 44 and the measurement object 14 are identical to those in the exemplary embodiment in accordance with FIG. 1. The portions of the OCT light reflected back from the measurement object 14 have thus passed through the λ/4 plate 30 twice. In this case, the λ/4 plate is oriented (rotated) such that the linear polarization state of the OCT light reflected back is orthogonal to the linear polarization state of the light that emerges from the exit end 45 of the third optical waveguide 44. This is typically the case if the angle between the linear polarization at the entrance into the plate and the crystal-optical axis of the plate is 45°. On account of the orthogonal polarization state, the OCT light reflected back enters the slow axis 61 of the third polarization-maintaining optical waveguide 44.

The object beam path 23 of the OCT light reflected back from the measurement object 14 continues through the first fiber coupler 40 into a first polarization-maintaining optical waveguide 46, which extends between the fiber coupler 40 and a second fiber coupler 47. The first polarization-maintaining optical waveguide 46 is connected to the first fiber coupler 40 such that the OCT light from the slow axis 61 of the third optical waveguide 44 passes over to the slow axis 61 of the first optical waveguide 46.

The reference beam path 24 extends through a second polarization-maintaining optical waveguide 48, which is arranged between the first fiber coupler 40 and the second fiber coupler 47 and which is subdivided into a first section 49 and a second section 50. The first section 49 and the second section 50 are connected to one another in a fiber connector 51, the second section 50 being rotated by 90° relative to the first section 49.

In the first fiber coupler 40, the light coming from the OCT light source 16 is guided into the fast axis 62 of the first section 49 of the second polarization-maintaining optical waveguide 48. Any transfer into the slow axis 61 of the second section 50 of the second optical waveguide 48 is effected in the fiber connector 51. The length of the first section 49 corresponds to the length of the third optical waveguide 44, such that the OCT light in the object arm and in the reference arm covers the same path distance in the fast axis 62. The length of the second section 50 of the second optical waveguide 48 corresponds to the sum of the lengths of the third optical waveguide 44 and the first optical waveguide 46, such that the path distance covered in the slow axis 61 is identical in the reference arm and in the object arm. The position of the reference point in the object beam path can be chosen by way of the length of the first section 49. The optical length of the first section 49 must then correspond to the sum of the optical length of the third optical waveguide 44 and double the optical path length from the exit point 45 to the reference point.

The interference signal from the object beam path 23 and the reference beam path 24 arises in the second fiber coupler 47. The interference signals from the second fiber coupler 47, which are phase-shifted by 180°, are picked up by two detectors 52, 53. The stationary portion of the signal can be eliminated by difference formation between the two detectors 52, 53, thus resulting in a useful signal with a high resolution. The difference between the photocurrents of the detectors 52, 53 is converted into a voltage and digitized. In this case, the interference signal for a tuning process of the OCT light source 16 is firstly digitized in a spectrally resolved manner and then transformed into a spatial signal. Sectional images of the measurement object 14 can be created by lateral deflection of the OCT beam by means of the scanning device 27, 28.

In this embodiment, too, the portions of the OCT light reflected back from the measurement object 14 and the parasitic reflections at the optical elements of the object arm 19 have mutually orthogonal polarization states. The OCT light transported in the slow axis 61 of the first optical waveguide 46 contributes maximally to the interference signal in the second fiber coupler 47, while the parasitic reflections transported in the fast axis 62 are found only minimally in the interference signal. The embodiment in accordance with FIG. 2 has the advantage that the polarization state of the OCT light is maintained as a result of the use of the polarization-maintaining optical waveguides 43, 44, 46, 48, independently of the bending state of the optical waveguides 43, 44, 46, 48. The elements of the OCT system can thus be moved relative to one another with deformation of the optical waveguides 43, 44, 46, 48, without the interference signal losing quality.

Figure 3:
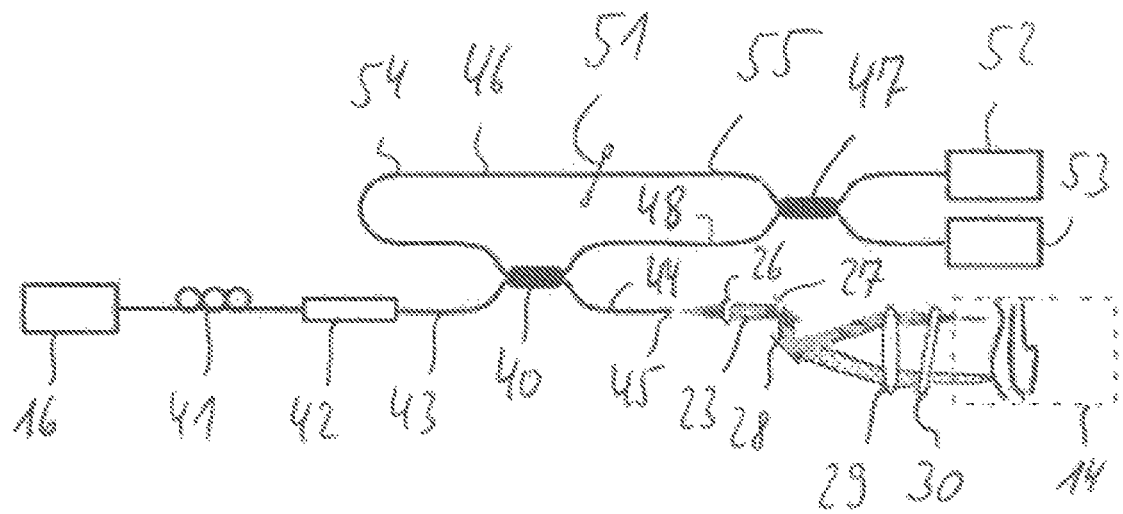
FIG. 3: shows a third embodiment of an OCT system according to the invention.

The embodiment in accordance with FIG. 3 differs from FIG. 2 in that the fiber connector 51 is arranged in the object beam path. The first polarization-maintaining optical waveguide 46 accordingly has a first section 54, in which the OCT light is transported in the slow axis 61, and a second section 55, in which the OCT light is transported in the fast axis 62. The lengths of the optical waveguides of the OCT system are coordinated with one another such that the reference point at which the lengths of the reference beam path 24 and of the object beam path 23 correspond lies just in front of the measurement object 14.

Figure 4:
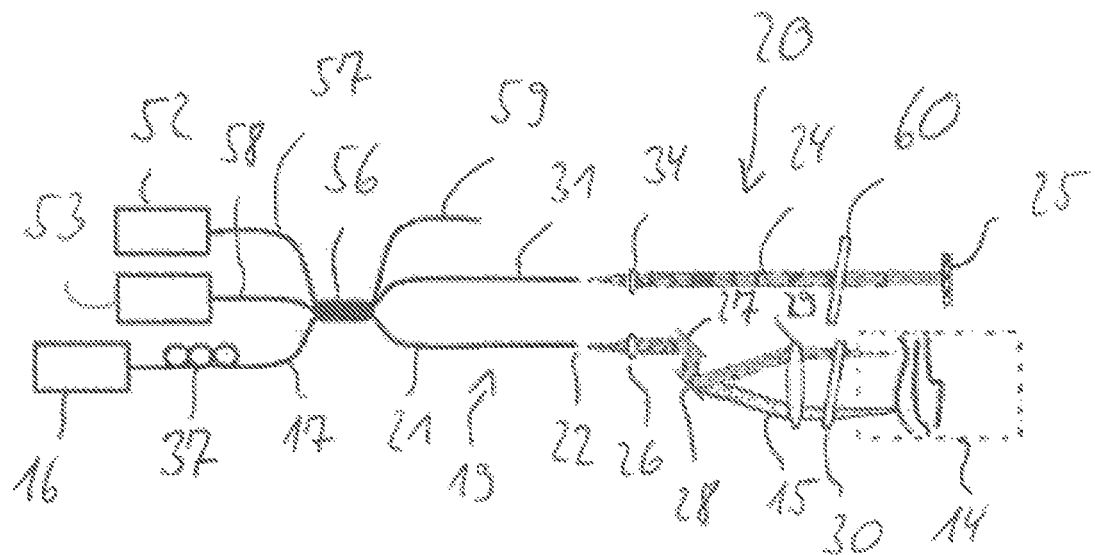
FIG. 4: shows a fourth embodiment of an OCT system according to the invention.
Figure 5:
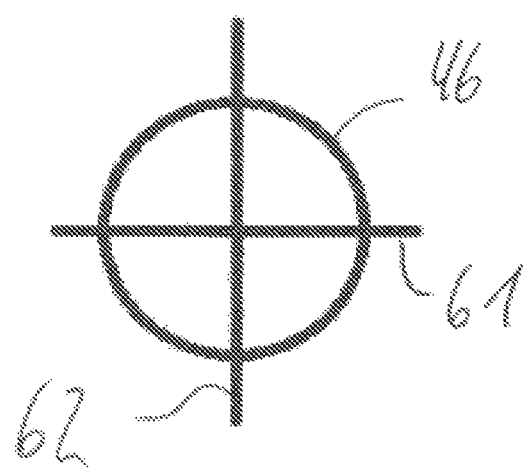
FIG. 5: shows a cross section through a polarization-maintaining optical waveguide.

In the embodiment in accordance with FIG. 4, a difference vis a vis FIG. 1 is that the OCT light 15 from the OCT light source 16 is fed into a 3×3 fiber coupler 56. As before the object 19 and the reference arm 20 are connected to the first two output channels of the 3×3 fiber coupler; the third output channel 59 remains unused. On the other side of the 3×3 fiber coupler 56, besides the OCT light source 16, two detectors 52, 53 are connected via optical waveguides 57, 58. A differential measurement as described above in the context of FIG. 2 can be carried out in this way. The optical waveguides 17, 21, 31, 57, 58 are non-polarization-maintaining single-mode fibers. A second polarization-dependent retardation element 60 is arranged in the reference beam path 24, and is oriented (rotated) in a manner matching the first polarization-dependent retardation element 30, such that the OCT light 15 backscattered from the measurement object 14 generates a maximum interference signal.

The invention claimed is:

1. An OCT system for examining a measurement object, comprising an OCT light source for emitting OCT light, comprising a polarization-neutral beam splitter for splitting the OCT light into an object beam path and a reference beam path, wherein the OCT light is polarized before entering the polarization-neutral beam splitter, and comprising a detector for picking up an interference signal generated from the object beam path and the reference beam path, wherein a polarization-dependent retardation element is arranged in the object beam path, wherein all optical elements that shape or deflect the object beam path on the path from the OCT light source to the measurement object are arranged between the OCT light source and the retardation element, wherein the light from the reference beam path is caused to interfere with light from the object beam path at an interference beam splitter, wherein the polarization state in the reference beam path is set such that the interference with the OCT light coming from the measurement object becomes maximal, wherein the polarization-dependent retardation element is configured such that at the interference beam splitter a polarization overlap between light backscattered from the measurement object and light arriving from the reference beam path is greater than a polarization overlap between light reflected by optical elements in the object beam path and the light arriving from the reference beam path, and wherein both the light backscattered from the measurement object and the light reflected by the optical elements in the object beam path are guided onto the detector and are detected by the detector.

2. The OCT system of claim 1, wherein the OCT light is polarized before entering the polarization-dependent retardation element.

3. The OCT system of claim 1, wherein the polarization-dependent retardation element is arranged such that the OCT light in the object beam path passes through it twice.

4. The OCT system of claim 1, wherein the polarization-dependent retardation element is a λ/4 plate.

5. The OCT system of claim 1, wherein an interface of the polarization-dependent retardation element facing the object is tilted relative to the object beam path.

6. The OCT system of claim 1, wherein said polarization-neutral beam splitter is a first beam splitter.

7. The OCT system of claim 6, wherein the interference signal is generated in the first beam splitter.

8. The OCT system of claim 6, wherein the interference signal is generated in a second beam splitter.

9. The OCT system of claim 8, wherein the reference beam path extends between the first beam splitter and the second beam splitter.

10. The OCT system of claim 1, wherein the OCT system comprises one or more optical waveguides embodied as polarization-maintaining optical waveguides.

11. The OCT system of claim 10, wherein a section of the object beam path extends in a polarization-maintaining optical waveguide, wherein the OCT light propagates in a first axis of the polarization-maintaining optical waveguide on an outgoing direction and propagates in a second axis of the polarization-maintaining optical waveguide on a return direction.

12. The OCT system of claim 10, wherein the reference beam path extends in a polarization-maintaining optical waveguide, wherein the OCT light extends in a first axis of the polarization-maintaining optical waveguide in a first section of the reference beam path and wherein the OCT light extends in a second axis of the polarization-maintaining optical waveguide in a second section of the reference beam path.

13. An OCT method for examining a measurement object, in which OCT light is emitted and is split into an object beam path and a reference beam path by a polarization-neutral beam splitter, wherein the OCT light is polarized before entering the polarization-neutral beam splitter, wherein an interference signal generated from the object beam path and the reference beam path is picked up by a detector, wherein the OCT light is guided through a polarization-dependent retardation element arranged in the object beam path, wherein all optical elements that shape or deflect the object beam path on the path from the OCT light source to the measurement object are arranged between the OCT light source and the polarization-dependent retardation element, wherein light from the reference beam path is caused to interfere with light from the object beam path at an interference beam splitter, wherein the polarization state in the reference beam path is set such that the interference with the OCT light coming from the measurement object becomes maximal, wherein the polarization-dependent retardation element is configured such that at the interference beam splitter a polarization overlap between light backscattered from the measurement object and-light arriving from the reference beam path is greater than a polarization overlap between light reflected by optical elements in the object beam path and the light arriving from the reference beam path, and wherein both the light backscattered from the measurement object and the light reflected by the optical elements in the object beam path are guided onto the detector and are detected by the detector.

* * * * *